United States Patent
Patwardhan

(10) Patent No.: US 8,394,099 B2
(45) Date of Patent: Mar. 12, 2013

(54) SURGICAL NAVIGATION

(75) Inventor: Ravish V. Patwardhan, Shreveport, LA (US)

(73) Assignee: Interactive Neuroscience Center, LLC, Shreveport, LA (US)

( * ) Notice: Subject to any disclaimer, the term of this patent is extended or adjusted under 35 U.S.C. 154(b) by 670 days.

(21) Appl. No.: 12/525,492

(22) PCT Filed: Feb. 1, 2008

(86) PCT No.: PCT/US2008/052790
§ 371 (c)(1),
(2), (4) Date: Jan. 6, 2010

(87) PCT Pub. No.: WO2008/095166
PCT Pub. Date: Aug. 7, 2008

(65) Prior Publication Data
US 2010/0114099 A1    May 6, 2010

Related U.S. Application Data

(60) Provisional application No. 60/887,719, filed on Feb. 1, 2007, provisional application No. 60/942,261, filed on Jun. 6, 2007.

(51) Int. Cl.
*A61B 17/00* (2006.01)
(52) U.S. Cl. .................................................... 606/80
(58) Field of Classification Search ............... 606/80, 606/96, 97
See application file for complete search history.

(56) References Cited

U.S. PATENT DOCUMENTS

| | | | |
|---|---|---|---|
| 4,362,161 A * | 12/1982 | Reimels et al. | 606/173 |
| 5,116,345 A | 5/1992 | Jewell et al. | |
| 5,800,557 A | 9/1998 | Elhami | |
| 7,780,679 B2 * | 8/2010 | Bobo et al. | 606/108 |
| 2002/0193800 A1 * | 12/2002 | Kienzle et al. | 606/80 |
| 2005/0065515 A1 | 3/2005 | Jahng | |
| 2006/0084867 A1 | 4/2006 | Tremblay | |
| 2006/0149280 A1 | 7/2006 | Harvie | |

FOREIGN PATENT DOCUMENTS

WO    WO 2006/078677    7/2006

OTHER PUBLICATIONS

Germano et al., "Clinical experience with intracranial brain needle biopsy using frameless surgical navigation," Comput Aided Surg., 1998, 3(1), pp. 33-39.

Kratimenos et al., "Multimodal imaging integration and stereotactic intracerebral electrode insertion in the investigation of drug resistant epilepsy," Acta Neurochir Suppl (Wien), 1993, 58, pp. 186-189.

(Continued)

*Primary Examiner* — Nicholas Woodall
(74) *Attorney, Agent, or Firm* — Quan & Associates; Nancy N. Quan

(57) ABSTRACT

A method of surgical navigation into' the brain includes establishing a trajectory through the skull into the brain to a target, drilling a hole in the skull using a drill (14), and verifying the trajectory of the drilled hole during drilling using image guidance. A surgical navigation system includes a cannulated drill, a cannulated access member (30), and a coupling member (16) for coupling the access member to the drill and for maintaining alignment of the cannulations in the drill and the access member. The access member is movable relative to the coupling member such that the access member can be secured to tissue while the coupling member maintains the alignment of the cannulations. A surgical kit includes a cannulated drill, a cannulated access member, a coupling member for coupling the access member to the drill, and a probe for receipt within the cannulated drill.

8 Claims, 5 Drawing Sheets

OTHER PUBLICATIONS

Kratimenos et al., "Stereotactic insertion of intracerebral electrodes in the investigation of epilepsy," Br J Neurosurgy, 1993, 7(1), pp. 45-52.

Lunsford et al., "Stereotactic implantation of deep brain electrodes using computed tomography," Neurosurgery, Sep. 1983; 13(3), pp. 280-286.

Heilbrun et al., "Preliminary experience using an optimized three-point transformation algorithm for spatial registration of coordinate systems: a method of noninvasive localization using frame-based stereotactic guidance systems," J Neurosurgy, Nov. 1994, 81(5), pp. 676-682.

Doshi et al., "Frameless stereotaxy and interactive neurosurgery with the ISG viewing wand," Acta Neurochir Suppl., 1995, 64, pp. 49-53.

Golfinos et al., "Clinical use of a frameless stereotactic arm: results of 325 cases," J Neurosurg., Aug. 1995, 83(2), pp. 197-205.

Tronnier et al., "Intraoperative computer-assisted neuronavigation in functional neurosurgery," Stereotact Funct Neurosurg., 1996, 66(1-3), pp. 65-68.

Dorward et al., "Clinical introduction of an adjustable rigid instrument holder for frameless stereotactic interventions," Comput Aided Surg., 1997, 2(3-4), pp. 180-185.

Eljamel, "Accuracy, efficacy, and clinical applications of the Radionics Operating Arm System," Comput Aided Surg., 1997, 2(5), pp. 292-297.

Kremser et al., "Image registration of MR and CT images using a frameless fiducial marker system," Magn Reson Imaging, 1997, 15(5), pp. 579-585.

Patel et al., "A simple trajectory guidance device that assists freehand and interactive image guided biopsy of small deep intracranial targets," Comput Aided Surg., 1997, 2(3-4), pp. 186-192.

Vinas et al., "Application accuracy study of a semipermanent fiducial system for frameless stereotaxis," Comput Aided Surg. 1997, 2(5), pp. 257-63.

Murphy, "An automatic six-degree-of-freedom image registration algorithm for image-guided fameless stereotaxic radiosurgery," Med Phys., Jun. 1997, 24(6), pp. 857-866.

Helm et al., "Accuracy of registration methods in frameless stereotaxis," Comput Aided Surg., 1998, 3(2), pp. 51-56.

Reinges et al., "Experience with a new multifunctional articulated instrument holder in minimally invasive navigated neurosurgery," Minim Invasive Neurosurgy, Sep. 1998, 41(3), pp. 149-151.

Van Roost et al., "Depth electrode implantation in the length axis of the hippocampus for the presurgical evaluation of medial temporal lobe epilepsy: a computed tomography-based stereotactic insertion technique and its accuracy," Neurosurgery, Oct. 1998, 43(4), pp. 819-826, discussion 826-827.

Eljamel, "Frameless stereotactic neurosurgery: two steps towards the Holy Grail of surgical navigation," Stereotact Funct Neurosurg., 1999, 72(2-4), pp. 125-128.

Kim et al., "New software applications for interchangeable instrumentation in spinal stereotaxis," Stud Health Technol Inform, 1999, 62, pp. 179-180.

Dorward et al., "Accuracy of true frameless stereotaxy: in vivo measurement and laboratory phantom studies. Technical note," J Neurosurg., Jan. 1999, 90(1), pp. 160-168.

Kim et al., "Universal calibration of surgical instruments for spinal stereotaxy," Neurosurgery, Jan. 1999, 44(1), pp. 173-177, discussion 177-178.

Steinmeier et al., "Factors influencing the application accuracy of neuronavigation systems," Stereotact Funct Neurosurg. 2000, 75(4), pp. 188-202.

Bernays et al., "A new artifact-free device for frameless, magnetic resonance imaging-guided stereotactic procedures," Neurosurgery. Jan. 2000, 46(1), pp. 112-6; discussion 116-117.

Kamimura et al., "Cervical pedicle screw insertion: assessment of safety and accuracy with computer-assisted image guidance," J Spinal Disord. Jun. 2000;13(3), pp. 218-224. Comment in: J Spinal Disord, Aug. 2000, 13(4), p. 275.

Muacevic et al., "Accuracy and clinical applicability of a passive marker based frameless neuronavigation system", J Clin Neurosci., Sep. 2000, 7(5), pp. 414-418.

Moriarty et al., "Frameless stereotactic neurosurgery using intraoperative magnetic resonance imaging: stereotactic brain biopsy," Neurosurgery, Nov. 2000, 47(5), pp. 1138-1145, discussion 1145-1146.

Benardete et al., "Comparison of frameless stereotactic systems: accuracy, precision, and applications," Neurosurgery. Dec. 2001, 49(6), pp. 1409-1415, discussion 1415-1416.

Gil et al., "Ventricular catheter placement in children with hydrocephalus and small ventricles: the use of a frameless neuronavigation system," Childs Nery Syst., Feb. 2002, 18(1-2), pp. 26-29, Epub Jan. 26, 2002.

Murphy et al., "Insertion of depth electrodes with or without subdural grids using frameless stereotactic guidance systems—technique and outcome," Br J Neurosurg., Apr. 2002;16(2), pp. 119-125.

Gralla et al., "Frameless stereotactic brain biopsy procedures using the Stealth Station: indications, accuracy and results," Zentralbl Neurochir., 2003, 64(4), pp. 166-170.

Dorward et al., "The advantages of frameless stereotactic biopsy over frame-based biopsy," Br J Neurosurg., Apr. 2002, 16(2), pp. 110-118. Comment in: Br J Neurosurg., Feb. 2003, 17(1), pp. 90-91, Author Reply 91.

Tirakotai et al., "Clinical application of neuro-navigation in a series of single burr-hole procedures," Zentralbl Neurochir., May 2004, 65(2), pp. 57-64.

Henderson, "Frameless localization for functional neurosurgical procedures: a preliminary accuracy study," Stereotact Funct Neurosurg. 2004, 82(4), pp. 135-141, Epub Oct 4, 2004.

Housepian, "Stereotactic surgery: the early years," Neurosurgery, Nov. 2004; 55(5), pp. 1210-1214.

Mehta et al.; "Frameless stereotactic placement of depth electrodes in epilepsy surgery," J Neurosurg. 2005 Jun., 102(6), pp. 1040-1045.

Smith et al., "Frame-based stereotactic biopsy remains an important diagnostic tool with distinct advantages over frameless stereotactic biopsy," J Neurooncol. Jun. 2005; 73(2), pp. 173-179.

Holloway et al., "Frameless stereotaxy using bone fiducial markers for deep brain stimulation," J Neurosurg., Sep. 2005, 103(3), pp. 404-413.

Spivak et al., "Comparison of the reliability of brain lesion localization when using traditional and stereotactic image-guided techniques: a prospective study," J Neurosurg., Sep. 2005, 103(3), pp. 424-427.

Woerdeman et al., "Frameless stereotactic placement of ventriculoperitoneal shunts in undersized ventricles: a simple modification to free-hand procedures," Br J. Neurosurg., Dec. 2005, 19(6), pp. 484-487.

Quinones-Hinojosa et al., "Assessment of image guided accuracy in a skull model: comparison of frameless stereotaxy techniques vs. frame-based localization," J Neurooncol., Jan. 2006, 76(1), pp. 65-70.

Woodworth et al., "Frameless image-guided stereotactic brain biopsy procedure: diagnostic yield, surgical morbidity, and comparison with the frame-based technique," J Neurosurg., Feb. 2006, 104(2), pp. 233-237.

Holly et al., "Percutaneous placement of posterior cervical screws using three-dimensional fluoroscopy," Spine, Mar. 1, 2006, 31(5), pp. 536-540; discussion 541.

Rachinger, J. et al., "Application accuracy of automatic registration in frameless stereotaxy," Stereotact Funct Neurosurg, 2006, 84(2-3), pp. 109-117, Epub Jul. 10, 2006.

Jung et al., "Application of neuronavigation system to brain tumor surgery with clinical experience of 420 cases", Minim Invasive Neurosurg., Aug. 2006, 49(4), pp. 210-215.

Mascott, C.R., "In vivo accuracy of image guidance performed using optical tracking and optimized registration," J Neurosurg., Oct. 2006, 105(4), p. 561-567.

Leung et al., "Practice of Intramedullary Locked Nails: New Developments in Techniques and Applications," Springer-Verlag, 2006, pp. 243-263.

International Search Report, PCT/US2008/052790, Jul. 2, 2008, 3 pages.

PCT International Preliminary Report on Patentability, and Written Opinion of the International Searching Authority, PCT/US2008/052790, Aug. 13, 2009, 9 pages.

Catalogue listing for Stryker 2102 Complete Set Orthopedic, 1 pages.

EPO Communication Pursuant to Article 94(3) EPC, dated Sep. 15, 2010, 5 pages.

* cited by examiner

SURGICAL NAVIGATION

CROSS-REFERENCE TO RELATED APPLICATIONS

This application is a National Stage of International Application No. PCT/US2008/052790, filed Feb. 1, 2008, which claims priority from U.S. Provisional Application No. 60/887,719, filed Feb. 1, 2007, entitled SURGICAL NAVIGATION and U.S. Provisional Application No. 60/942,261, filed Jun. 6, 2007, entitled SURGICAL NAVIGATION, which are incorporated by reference herein in their entirety.

TECHNICAL FIELD

This invention relates to surgical navigation.

SUMMARY

A method of surgical navigation into the brain includes establishing a trajectory through the skull into the brain to a target, drilling a hole in the skull using a drill, and verifying the trajectory of the drilled hole during drilling using image guidance.

Embodiments of this aspect may include one or more of the following features. The image guidance is provided by a probe received by the drill. The probe is received in a lumen defined by the drill. The method includes placing an access member in the drilled hole, and verifying the trajectory of the access member during placement. The access member is placed using the drill, and the trajectory is verified using the probe received by the drill.

A surgical navigation system includes a cannulated drill, a cannulated access member, and a coupling member for coupling the access member to the drill and for maintaining alignment of the cannulations in the drill and the access member. The access member is movable relative to the coupling member such that the access member can be secured to tissue while the coupling member maintains the alignment of the cannulations.

Embodiments of this aspect may include one or more of the following features. The system includes a probe for receipt within the cannulated drill. The system includes a drill bit.

A surgical kit includes a cannulated drill, a cannulated access member, a coupling member for coupling the access member to the drill, and a probe for receipt within the cannulated drill. Embodiments of this aspect may also include a drill bit, a medical device, and/or a robot arm.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
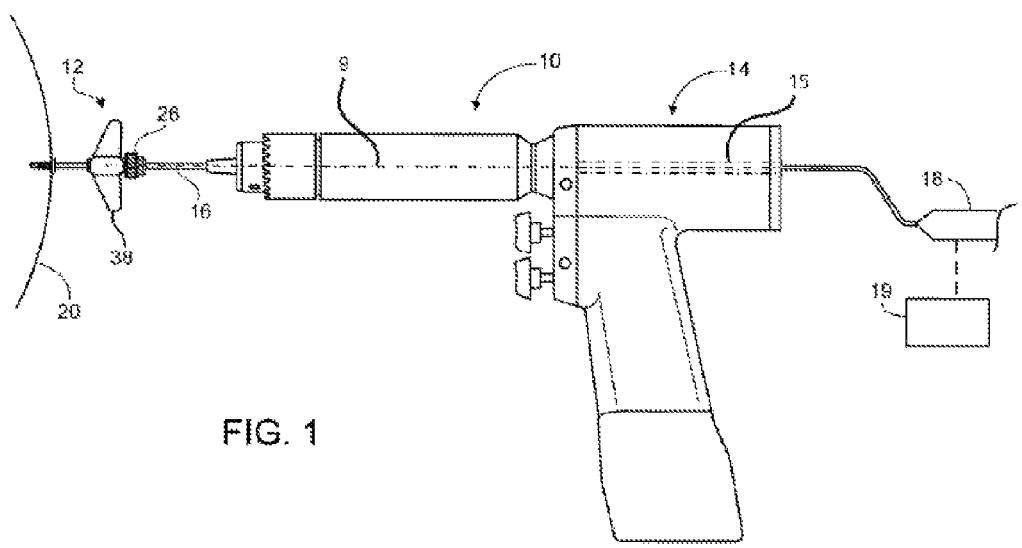
FIG. 1 is an illustration of a cannulated drill being used to place an access member in the skull under navigation guidance.

Referring to FIG. 1, an image-guided trajectory system 10 includes an access member 12 for establishing a set trajectory 9 to a target site, a cannulated drill 14, and a coupling member rod 16 that couples the access member 12 to the cannulated drill 14 during securement of the access member 12 to a patient's skull 20. Also shown in FIG. 1 is a probe 18, for example, a BrainLab Probe (available from BrainLab Cranial Navigation System) or an Integra Probe (available from Integra LifeSciences), received within the drill 14, for example, within a cannulation or lumen defined by the drill 14, such as internal lumen 15 along trajectory 9 as illustrated, and extending about half-way down the length of the drill 14. The probe 18 is coupled to an image guidance system 19, for example, a BrainLab image guidance system or an Integra image guidance system, which tracks the trajectory of the probe 18 relative to images of a patient's brain. The receipt of the probe 18 within the cannulated drill 14 during securement of the access member 12 to the skull 20 insures that the access member 12 establishes the desired trajectory to a target site.

Figure 2:
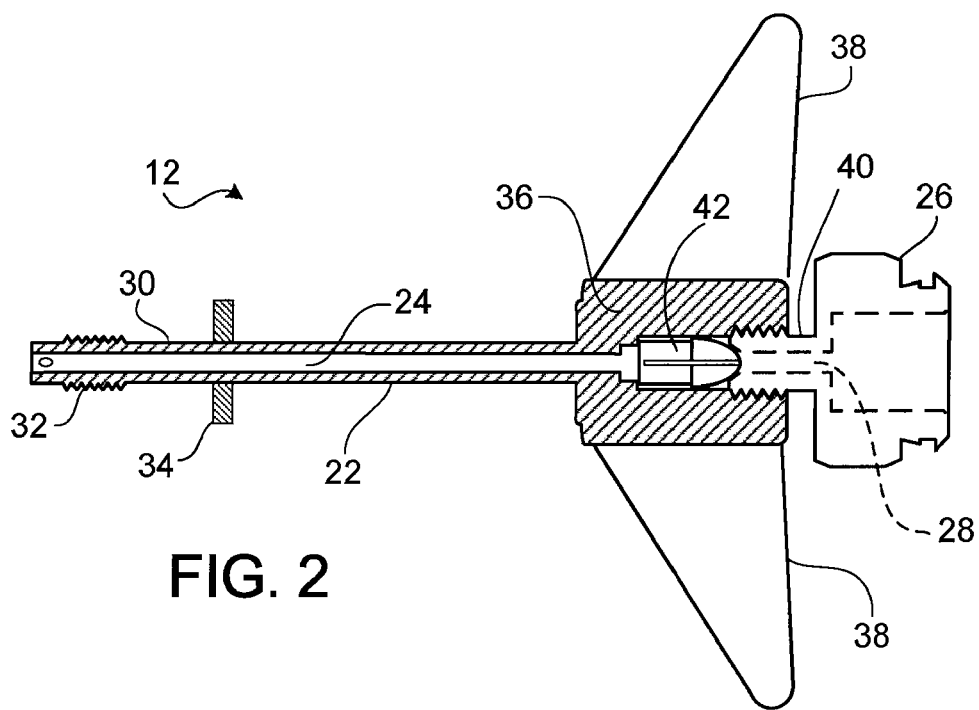
FIG. 2 is a partial cross-sectional view of the access member.

Referring to FIG. 2, the access member 12 includes a main body 22 defining an internal lumen 24, and a clamping member 26 defining an internal lumen 28 aligned with lumen 24. The main body 22 has a distal portion 30 with a threaded region 32 that engages the skull bone to secure the access member to the skull 20. Surrounding the distal portion 30 is a depth stop 34 that sets the depth to which the access member 12 is insertable into the skull. The main body 22 has a proximal portion 36 with two outwardly extending wings 38 that can be engaged by the operator's hand and turned to thread the access member 12 into the skull.

Figure 3:
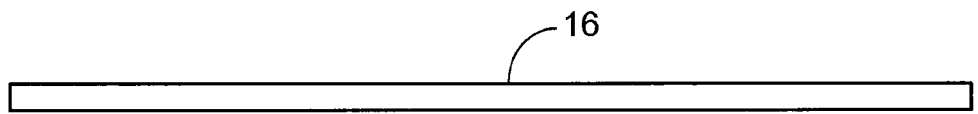
FIG. 3 is a side view of a coupling member that couples the access member to the cannulated drill.

The clamping member 26 has a threaded extension 40 that is received by the proximal portion 36 of the main body 24 and is rotatable relative to the main body 24. The clamping member 26 acts on a collet 42 located within proximal portion 36 such that rotation of the clamping member 26 causes the collet 42 to clamp onto and release the rod 16 (FIG. 3) received in the lumens 24 and 28.

Figure 4:
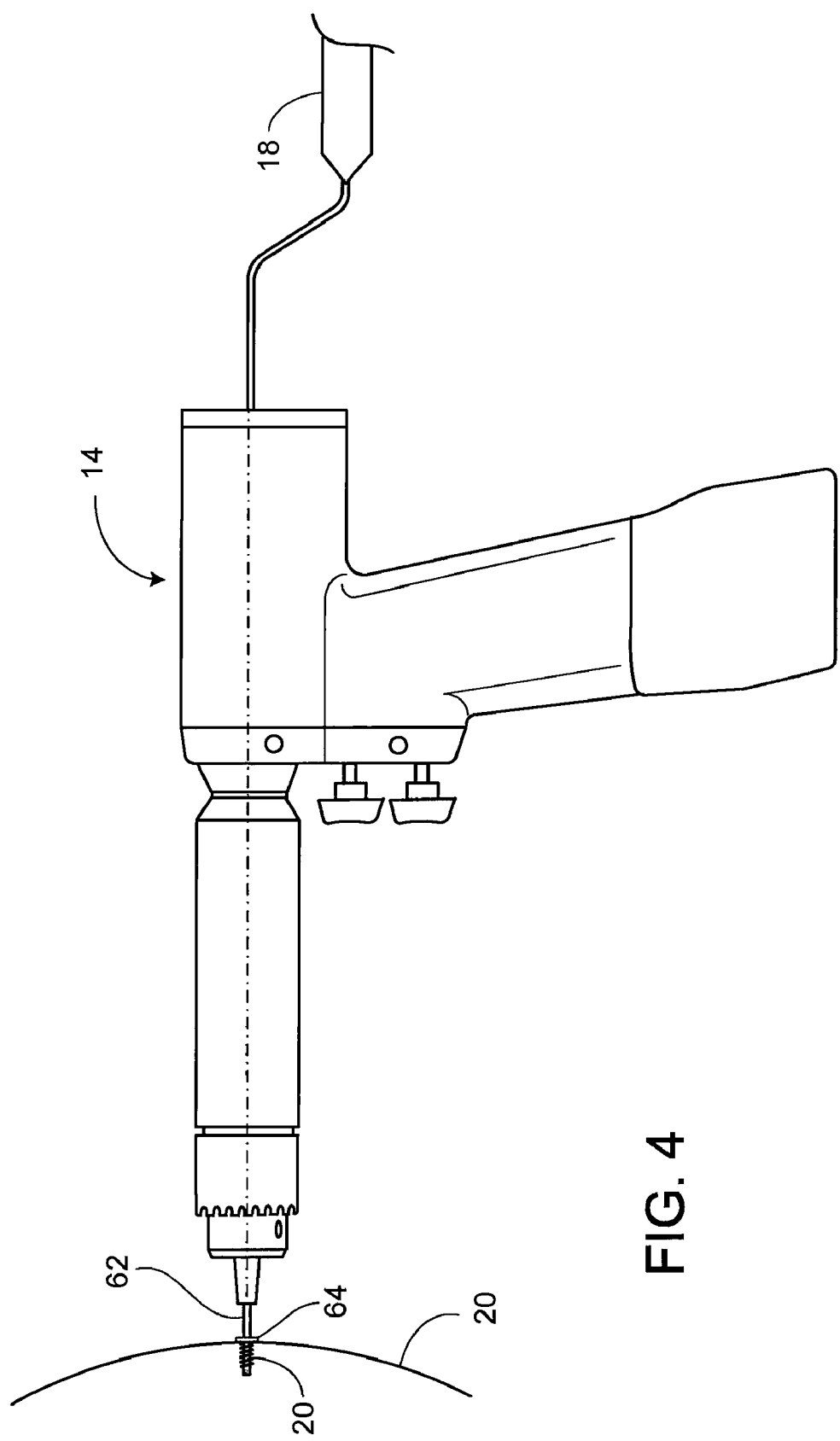
FIG. 4 shows the cannulated drill being used to drill a hole in a skull.

Referring to FIG. 4, prior to securing the access member 12 to the skull 20, the operator uses the cannulated drill 14 to drill a pilot hole 60 in the skull 20. Using a drill bit 62 and with the probe 18 received within the drill 14, the operator drills the pilot hole 60 under image guidance such that the pilot hole 60 is aligned with a desired preplanned trajectory to a target set within the brain. Surrounding the drill bit 62 is a movable depth stop 64 that sets the depth to which the drill bit 62 is insertable into the skull.

After drilling the pilot hole, the operator replaces the drill bit 62 with the rod 16 and attached access member 12, a shown in FIG. 1. The rod 16 extends about 3.5 cm into the drill 14 and about 3.5 cm into the access member 12 to axially align the drill 14 and the access member 12. The operator places the access member 12 against the entrance to the pilot hole 60 and uses the probe 18 to align the access member 12 along the desired trajectory to the target site. The operator then loosens the collet 26 such that the access member 12 can be rotated relative to the rod 16 to advance the access member 12 into the skull 20. While the rod remains attached to the drill 14 and remains within the lumens 24, 28 during rotation of the access member 12, the rod 16 need not move, that is, is not rotated, during the advancement of the access member 12.

While applying a force to the wings 38 to thread the access member 12 into the skull 20, the operator verifies the alignment of the access member 12 along the trajectory using probe 18 positioned within drill 14.

Figure 5:
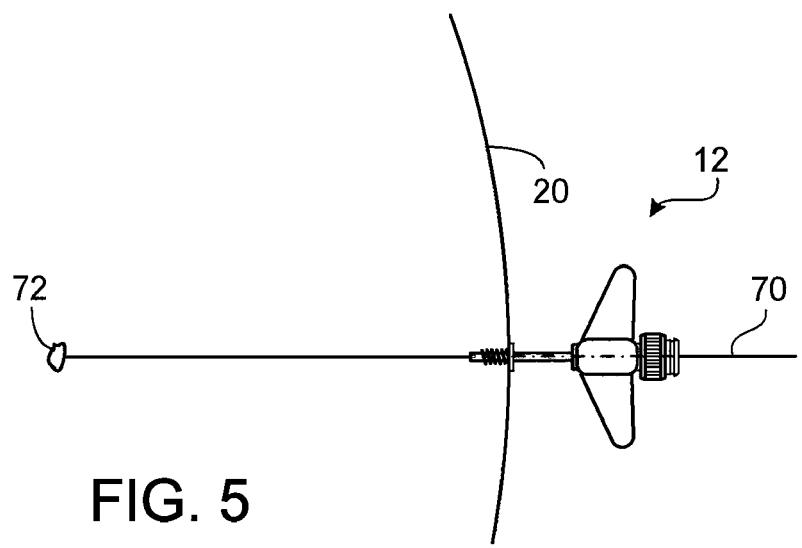
FIG. 5 shows the access member being used to position a medical device at a target site within the brain.

The operator then removes the drill 14 and rod 16 from the access member 12. Referring to FIG. 5, the access member 12 now establishes a set trajectory for introduction of various medical devices 70, e.g., ventriculostomy catheters, other directed catheters for convection therapy, epilepsy depth electrodes, thermocoagulation probes, lesioning probes, stereotactic needles, and ablative probes, to the target site 72. The operator need only control the depth of advancement of the medical device, which, in many cases, can be predetermined using navigation software.

To further increase the accuracy of the device placement through the access member 12, the drill 14 can directly hold the access member after securement of the access member to the skull 20, and the medical device can be passed through the drill and the access member to the target site.

A cannulated drill is available from Stryker (4200 Cordless Driver 2), and can be used with a step down chuck for holding the drill bit 62 and the rod 16.

Figure 6:
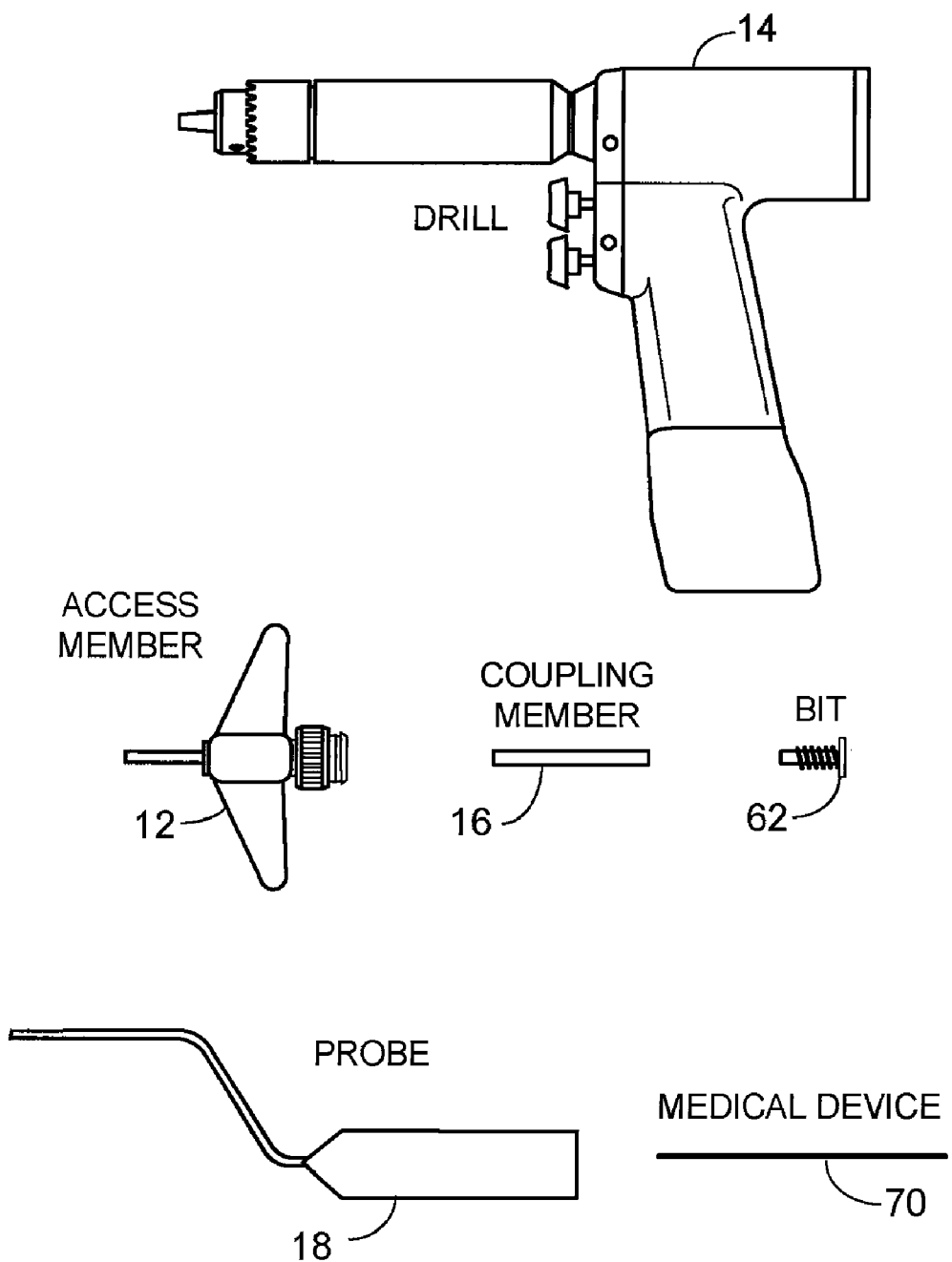
FIG. 6 illustrates an exemplary disposable kit containing components of the system.

The various components of the image-guided trajectory system 10 can be sold as kits 80 (FIG. 6), either disposable or non disposable, including one or more components of the system 10. For example, the cannulated drill 14, the access member 12, the coupling member 16, and the drill bit 62 can be packaged together for sale as a disposable kit. Alternatively, any combination of one or more of the four components can be packaged together for sale as a disposable kit, for example, just the access member 12, the coupling member 16, and the drill bit 62 can be packaged together, the access member 12 and the coupling member 16 can be packaged together, etc. The probe 18 can also be included in any of the various combinations of disposable kits described above, for example, a disposable kit can include the probe 18, drill 14, access member 12, and coupling member 16. Furthermore, one or more medical devices 70 can be included in any of the various combinations of disposable kits, including kits with the probe 18. All of the components need not be disposable. The various components can be sold as a system with the image guidance system 19.

Figure 7:
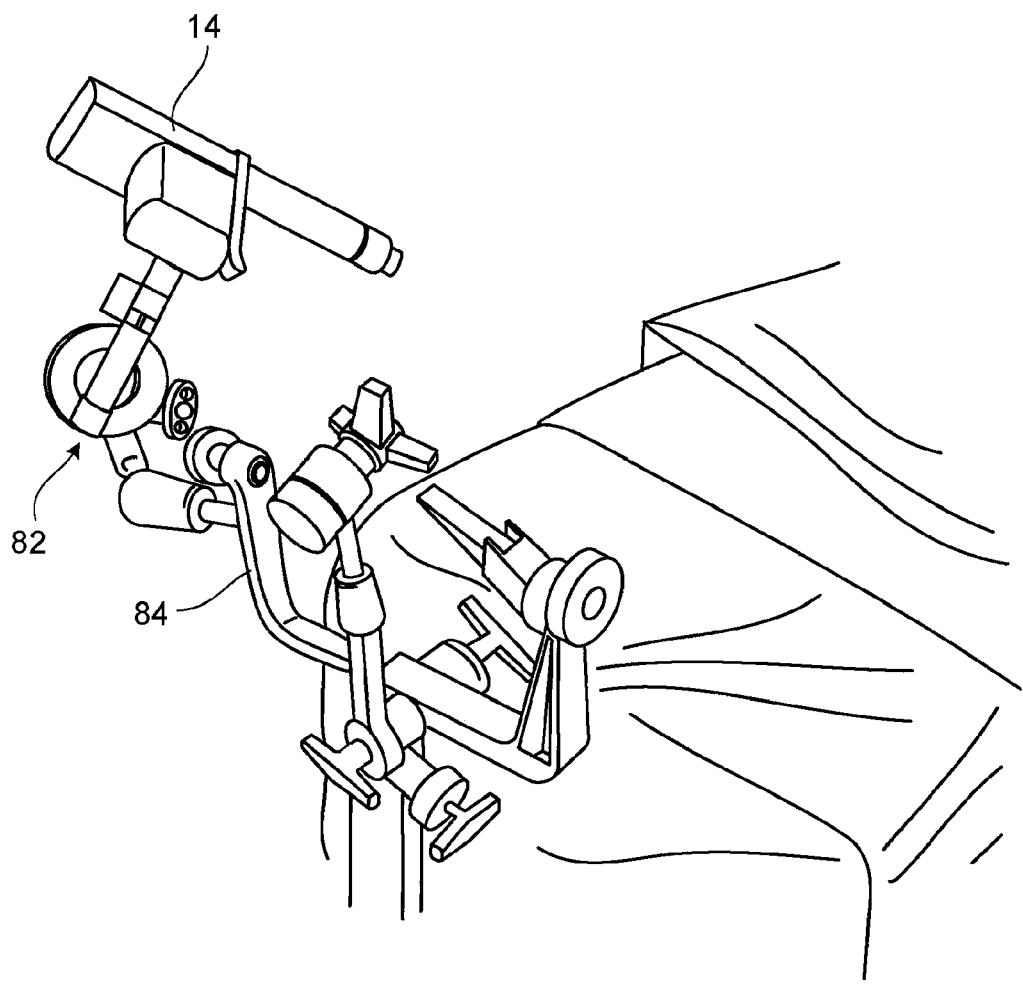
FIG. 7 illustrates a robot arm supporting the cannulated drill.

Referring to FIG. 7, the cannulated drill 14 can be supported during use by a robot arm 82, for example, a BrainLab robot arm. The robot arm 82 can be manipulated to fix the position of the cannulated drill 14 in a selected axis. The robot arm 82 is preferably supported by a device 84, for example, a Mayfield head holder, used to fixate the head. The robot arm 82 can be included in any of the kit configurations described above.

Various modifications may be made without departing from the spirit and scope of the invention. Accordingly, other embodiments are within the scope of the following claims.

What is claimed is:

1. A method comprising:
   establishing a trajectory through the skull into the brain to a target,
   drilling a hole in the skull using a drill,
   verifying the trajectory of the drilled hole during drilling using image guidance provided by a probe received by the drill, and
   placing an access member in the drilled hole using the drill,
   verifying the trajectory of the access member during placement using a probe received by the drill.

2. The method of claim 1 wherein the drill defines a lumen.

3. The method of claim 2 wherein the probe is received in the lumen defined by the drill.

4. The method of claim 1, further comprising placing a medical device in a lumen defined by the access member.

5. The method of claim 4, further comprising securing the medical device in the access member.

6. The method of claim 4, wherein the medical device is selected from a group consisting of a ventriculostomy catheter, convention therapy catheter, epilepsy depth electrode, thermocoagulation probe, lesioning probe, stereotactic needle and ablative probe.

7. The method of claim 1, wherein the probe is tracked by navigation software.

8. The method of claim 7, wherein said navigation software tracks the probe relative to images of a patient's body.

* * * * *